(12) United States Patent
Han

(10) Patent No.: US 6,444,236 B1
(45) Date of Patent: Sep. 3, 2002

(54) COMPOSITON CONTAINING MEDICINAL HERBS AND YOUNG ANTLERS OF CORNU CERVI

(76) Inventor: Wan-Seok Han, #610-4, Shinsa-dong, Kangnam-ku, 135-894, Seoul (KR)

(*) Notice: Subject to any disclaimer, the term of this patent is extended or adjusted under 35 U.S.C. 154(b) by 0 days.

(21) Appl. No.: 09/938,549

(22) Filed: Aug. 27, 2001

(51) Int. Cl.⁷ .................. A01N 63/00; A01N 65/00; A61K 35/32
(52) U.S. Cl. .............. 424/725; 424/93.7; 424/549; 424/770; 424/777; 426/531
(58) Field of Search ............... 424/93.7, 725, 424/777, 549, 770; 426/72, 531, 541, 21

(56) References Cited

U.S. PATENT DOCUMENTS 5,466,443 A * 11/1995 Ho et al. ............... 424/70.6
6,271,001 B1 * 8/2001 Clarke et al. ............... 435/72

* cited by examiner

Primary Examiner—David M. Naff
Assistant Examiner—Deborah K. Ware
(74) Attorney, Agent, or Firm—Nath & Associates PLLC; Gary M. Nath; Joshua B. Goldberg

(57) ABSTRACT

A composition is provided for use in health foods for promoting the circulation of blood, prepared from medicinal herbs, including *Lycium chinense* Miller, *Agastache rugosa* (Fischer et Meyer) O. Kuntze, *Pueraria lobat* Ohwi, Macrocarpium officinale Sieb. et Zucc., *Gastrodia elata blume*, *Amomum xanthioides* Wallich, *Cratagegus pinnatifida* Bge., Aquillaria Agallocha Roxburgh, *Inula Helenium* L., *Cassia obtusifolia* L., and *Rubus sachalinensis* Lev., and young antlers of *Cornu cervi*. In addition to being safe to the body, the composition exhibits excellent pharmaceutical effects of treating arteriosclerosis and alleviating the headache attributed to the disturbance of blood circulation.

1 Claim, No Drawings

COMPOSITON CONTAINING MEDICINAL HERBS AND YOUNG ANTLERS OF CORNU CERVI

FIELD OF THE INVENTION

The present invention relates, in general, to a composition of health foods for promoting the circulation of blood and, more particularly, to a composition made of medicinal herbs, *Lycium chinense* Miller, *Agastache rugosa* (Fischer et Meyer) O. Kuntze, *Pueraria lobat* Ohwi, Macrocarpium officinale Sieb. et Zucc., *Gastrodia elata blume, Amomum xanthioides* Wallich, *Cratagegus pinnatifida* Bge., Aquillaria Agallocha Roxburgh, *Inula Helenium* L., *Cassia obtusifolia* L., and *Rubus sachalinensis* Lev., and young antlers of *Cornu cervi*, suitable for use in health foods helpful in improving blood circulation.

DESCRIPTION OF THE PRIOR ART

At present, various electrical and electronic instruments are generally used in offices for office automation and even in home for home automation. On the whole, such instruments require the user to assume certain postures, for example, to maintain his or her arms at a distance from the body, for their operation. Accordingly, after operating the instruments for a long time of period, the user is liable to undergo stiffness at certain body sites, such as arms, legs, waist, etc. In most cases, stiffened muscles can be easily relieved simply by massaging them. However, once afflicted with muscular stiffness, those who operate such instruments every day have difficulty in healing the discomfort or pain.

In addition to the operation of OA instruments, exercise, physical work, inappropriate posture, and metal stress are found to cause muscular stiffness. Other causes of muscular stiffness are exemplified by cervical spondylosis, thoracic outlet syndrome, hypertension, asthenopia, autonomous dysmyotonia, and menoposal disorder. Symptoms of the stiffness include characteristic chronic pain, irritability, and, in severe cases, headache and emesis.

The circulation of blood is the movement of blood, driven by the heart, throughout the body through defined channels and tissue spaces, performing a variety of functions, including carrying oxygen to tissues and releasing carbon dioxide to the lungs, supplying nutrients, taking away metabolites from cells, transporting hormones from various endocrine glands to control the functions of tissues, immune activity, and controlling body temperature, osmosis, and water content, etc.

Blood vessels are classified into arteries, veins and capillaries. Arteries can be broken down into: tunica interna composed of simple asquamous epithelium, subcutaneous layer, and internal elastic lamina; tunica media composed of smooth muscle and elastic tissue; and tunica advantitia composed mostly of fibrous connective tissue. Serving as exchange vessels for nutrients, waste and fluids, and connecting the arteries and veins, capillaries carry blood from the arterioles to the venules. With a diameter of as small as 0.008–0.02 mm, capillaries are invisible and allow only one or two rows of red blood cells to pass therethrough. Forming nets, capillaries are composed of tunica interna only. Veins are separated into: tunica interna composed of an internal layer comprising valves for preventing the retrograde movement of blood; tunica media composed of smooth muscle, which is thin in veins; and tunica externa which is a heavy layer in many veins.

Circulatory disturbance, meaning an uneven movement of blood through vessels, is caused by narrowing of the lumen of non-elastic vessels, owing mainly to deposition of cholesterol therein. In many cases, circulatory disturbance leads to circulatory diseases. Of them, cerebral apoplexy is representative, which is caused by the rupture or occlusion of cerebral vessels. Cerebral apoplexy is classified into hemorrhagic apoplexy and ischemic apoplexy. Causes of a sudden onset of intracranial hemorrhage or bleeding are hypertension, aneurysm, bleeding into a tumor, and the like. Hemorrhagic apoplexy is subclassified into cerebral hemorrhage and subarachnoid hemorrhage. Ischemic apoplexy is caused by ischemia or inability to obtain necessary amounts of oxygen for the needs of the brain tissues, owing usually to the narrowing or blockage of a major or smaller crucial artery in the brain. Ischemic apoplexy is further classified into cerebral infarction and transient ischemic attack.

General causes of cerebral hemorrhage are hypertension and arteriosclerosis. Hypertension is a disorder characterized by high blood pressure; generally this is characterized by systolic blood pressure consistently higher than 140, or diastolic blood pressure consistently over 90. Hypertension is subclassified into mild hypertension with a diastolic blood pressure of 90 to 104, moderate hypertension with a diastolic blood pressure of 105 to 110, and heavy hypertension with a diastolic blood pressure of higher than 110. As much as 90% of all hypertension patients suffer from essential (primary) hypertension, which means that the high blood pressure has no identifiable cause. The rest comprise consecutive (secondary) hypertension sufferers whose cause is identifiable. On the whole, older persons tend to have higher blood pressures. Some research results disclose the hereditary nature of hypertension. Impatient persons are liable to suffer from hypertension. Obesity, salt ingestion, mental stresses, smoking, drinking, renal diseases, pheochromocytoma, use of oral contraceptives, and primary aldosteronemia are found to be causes of hypertension.

Arteriosclerosis is a vascular disease of the arteries in which fatty materials are deposited on vessel walls, resulting in narrowing of the vessel lumen and eventual impairment of blood flow. The elderly are more liable to be afflicted with arteriosclerotic diseases. Once a person suffers from arteriosclerosis, there occurs dysfunction of of various organs of his or hers. When it occurs at cerebral vessels, apoplexy results.

Additionally, heart diseases and diabetes mellitus are also associated with hypertension and/or arteriosclerosis.

Muscle stiffness, even though its etiology is not established firmly, is found to be attributed, at least in part, to the excessive contraction of peripheral vessels and circulatory disturbance and congestion within muscles, which result from excessive stimulation of nerves, muscle fatigue and/or autonomous dysmyotonia. Accordingly, relieving muscle stiffness is an effective way to improve blood circulation. With other therapies, such as massaging, warm-bath therapy, fomentation, electric stimulation and pharmacotheraphy, a desirable healing effect is difficult to obtain. In addition, some of these therapies are annoying because the patients have to go specialized hospitals.

SUMMARY OF THE INVENTION

Leading to the present invention, the intensive and thorough research to develop health foods for promoting the circulation of blood, conducted by the present inventor aiming to overcome the problems encountered in prior arts, resulted in the finding that certain wild herbs promote the functions of the organs relevant to the circulation of blood, and are medicinally effective for the treatment of arteriosclerosis and disturbance of blood circulation.

Therefore, it is an object of the present invention to provide a composition of health foods for promoting the circulation of blood, which is safe to the body and effective for treating diseases attributed to the disturbance of blood circulation.

In accordance with the present invention, the above object could be accomplished by a provision of a composition of health foods for promoting the circulation of blood, comprising: 5–13 wt % of *Lycium chinense* Miller, 5–13 wt % of young antlers of *Cornu cervi*, 5–13 wt % of *Agastache rugosa* (Fischer et Meyer) O. Kuntze, 5–13 wt % of *Pueraria lobat* Ohwi, 4–12 wt % of Macrocarpium officinale Sieb. et Zucc., 4–12 wt % of *Gastrodia elata blume*, 4–12 wt % of *Amomum xanthioides* Wallich, 4–12 wt % of *Cratagegus pinnatifida* Bge., 4–12 wt % of Aquillaria Agallocha Roxburgh, 4–12 wt % of *Inula Helenium* L., 4–12 wt % of *Cassia obtusifolia* L., and 4–12 wt % of *Rubus sachalinensis* Lev.

DETAILED DESCRIPTION OF THE INVENTION

The present invention pertains to a composition for use in health foods for promoting the circulation of blood, prepared from medicinal herbs, including *Lycium chinense* Miller, *Agastache rugosa* (Fischer et Meyer) O. Kuntze, *Pueraria lobat* Ohwi, Macrocarpium officinale Sieb. et Zucc., *Gastrodia elata blume, Amomum xanthioides* Wallich, *Cratagegus pinnatifida* Bge., Aquillaria Agallocha Roxburgh, *Inula Helenium* L., *Cassia obtusifolia* L.., and 4–12 wt % of *Rubus sachalinensis* Lev., and young antlers of *Cornu cervi*, Fruits of *Lycium chinense* Miller contain vitamins and zeaxanthine. Recently, scopletin, a biologically active material, has been isolated from the fruits. Also, there were isolated carotenoid and sterin, which are identified as physalien and β-sitosterin, respectively. In Oriental medicine, the fruits of *Lycium chinense* Miller are utilized as a hypotensive agent. Found to have the function of lowering blood cholesterol, the fruits are used for the prophylaxis and treatment of arteriosclerosis. In some historical medical books, the fruits are described to be useful for the treatment of lumbago, asthenia, vertigo, headache, and diabetes mellitus. It is also described that humans who have been administered with the fruit for a long period of time may enjoy medicinal effects including increased bone density, vigor, keen eyesight, resistance to cold and heat, and longevity.

Fruits of Macrocarpium officinale Sieb. et Zucc. contain crystalline organic acids, gallic acid, malic acid, tartaric acid, etc. In the skin of the fruits are found morroniside, loganin and sworoside. In Oriental medicine, the fruits are used to aid renal function and applied to persons who often sweat or urinate in small amounts, or suffer from lumbago or irregular menstruation.

Young antlers of the deer *Cornu cervi* are medicinally useful In Oriental medicine. For use in medicine, young antlers which have not yet keratinized are dried. Like ginseng, dried antlers are widely used in Oriental medicine. From young antlers, free amino acids, hexosamine acid, uronic acid, sialic acid, hypoxanthine estrone, and estradiol receptors are isolated. Many historical medical books describe that young antlers have a variety of potent medicinal effects, including invigoration, promotion of growth and development, hematosis, and promotion of functions of almost all organs, such as heart, liver, spleen, lungs, kidneys, gall bladder, stomach, intestines, paunch, bladder and bowels, immunological enhancement, and improvement of mental operation. In order to build up one's health and restore one's energy, young antlers are also used. In addition, young antlers are described to be useful for the treatment of neurasthenia and heart failure.

*Agastache rugosa* (Fischer et Meyer) O. Kuntze is a perennial plant growing to a height of 1–1.5 m. Consisting of methylcarbicol?, anisaldehyde, anethol, d-limonene, cescuiterpene, α-pinene, β-pinene, α-limonene, oxanone, P-cymol, and linalol, essential oils are isolated in an amount of about 0.3% from the whole herb, in an amount of about 0.2 to 2.3% from leaves, in an amount of 5% from flowers, and in an amount of 0.1% from stems. Also, there are isolated flavonoids, including acacetine, tilianin, linalin, and agastachoside. In Oriental medicine, the herb is used as a stomachic, a carminative, a digestive, or an antipyretic and administered to persons who suffer in hot weather, have an upset stomach, a cold, a headache, or who suffer from emesis and diarrhea. Additionally, the herb is often prescribed to treat cortical diseases and tumors. Particularly, it is essentially used for the treatment of spleen and stomach diseases.

Young *Gastrodia elata blume* grows by ingesting nutrients from its progenitor. The herb is especially prescribed for those who suffer from paralysis, children's seizures, headache, and nerve diseases. From the tuberous roots of *Gastrodia elasta blume*, p-hydroxybenzylalcohol and its glycoside gastrodine, and p-hydroxybenzylaldehyde are isolated. In Oriental medicine, young *Gastrodia elasta blume* is used as a tonic, a sedative and a contraparetic for the treatment of giddiness, nausea, epilepsy, neurasthenia, vomiting, and neuropathic aphasia, convulsions and paralysis of the limbs, and peripheral neuropathy. It is described in historical medical books that young *Gastrodia elasta blume* the herb is particularly beneficial to the nervous system and has a hematic function. In addition, the herb is used as a drug for treating nephritis, diabetes mellitus, hypertension, dysgonesis, physical fatigue, etc.

*Amomum xanthioides* Wallich is a perennial herb, which grows to a height of 1.3–2 m. Its fruits are used as a drug to treat stomachache, dyspepsia, nausea and diarrhea. It is administered at a single dosage of 2–3 g.

Like fruits of *Chaenomeles sinensis*, fruits of *Cratagegus pinnatifida* Bge. show a medicinal function of promoting urination because of their containing cuelcetine and oleanoic acid. Also, fruits of *Cratagegus pinnatifida* Bge. are found to contain vitamin B, C, carotin, and chlorogenic acid. In Oriental medicine, the fruits are applied to humans who suffer from postpartum abdominal pain, hangover, dyspepsia, or diarrhea. Particularly, the fruits are used as a stomachic.

Aquillaria Agallocha Roxburgh is an evergreen that is 30 m high. Its lignum part has no resinous materials normally, but when the tree is damaged, they are secreted from the lignum part to heal the wound. Lignum aloes is obtained by cutting the tree having the resinous materials and letting it rot naturally on the ground, followed by removing non-resinous parts to leave resinous parts. Essential oils can be obtained at a yield of 13% by the saponification with alkali and steam distillation of the lignum aloe. In Oriental medicine, the essential oils are used in a single dose of 1.5–3 g for the treatment of nausea, stomachache and asthma. In addition, the heartwood is used as a stomachic and a carminative.

*Inula Helenium* L. is a perennial herb, which grows to a height of 50 to 150 cm. From the roots of the herb, essential oils are obtained at a yield of 1 to 5%. When the essential oils are cooled, crystals are formed, called helenine. In addition to the crystals, the essential oils contain damiradienylacetate $C_{32}H_{52}O_2$, a kind of triterpene alcohol, a small amount of alantol $C_{15}H_{23}O_2$, and proazulene. From the roots, inulin, pseudo-inulin, inulenin, saponin, bitter substance, dyes, and a trace amount of alkaloids are isolated. Alantol is found in fresh roots. In Oriental medicine, the herb is used as an expectorant, a stomachic, a diuretic and a hidrotic for the treatment of various respiratory diseases such as catarrhal inflammation of the upper trachea, bronchitis, pulmonary tuberculosis, etc. It is also applied to those who suffer from vomiting, diarrhea, stomachache, catarrhal inflammation of the stomach, sour stomach, and cold.

Roots of *Pueraria lobat* Ohwi contain isoflavones such as daidsein $C_{15}H_{10}O_4$ and daidzin $C_2H_{20}O_9$, puerarin $C_2H_{20}O_9$, puerarin-xyloside, luteolin, biocanin, starch, and coumarin. In addition, choline, acetylcholine, cacneconem, cachkonein and puerarol are also obtained from the roots. In Oriental medicine, the roots are used as a perspiratory antipyretic and a contraparetic for the treatment of fever, dry throat, headache, tonsillitis, and acute tympanitis. Other medicinal effects of the roots include soothing neck stiffiess and shoulder stiffness and healing wounds. Disorders for which the roots are applicable are exemplified by extravasated blood, hypertension and tinnitus.

Seeds of *Cassia obtusifolia* L. contain emodin, obtusifolin, obtusin $C_{18}H_{16}O_7$, chryso-obtusin $C_{19}H_{18}O_7$, aurantio-obtusin $C_{17}H_4O_7$, and glycosides thereof Water or alcohol extracts of the seeds were found to have a hypotensive function as measured in animal tests. In Oriental medicine, the seeds are prescribed for the protection of the kidneys, the promotion of hepatic function, the prevention of paralysis, the alleviation of fever, and the treatment of headache and eye diseases.

Fruits of *Rubus sachalinensis* Lev. are rich in organic acids, such as lemon acid, salicylic acid, capronic acid, formic acid, and their salts. Also, the fruits are found to contain pectin, carotin (0.3 mg %), vitamin B, glucose at an amount of 4.3%, fructose at an amount of 8%, sucrose at an amount of 6.5%, tannmin at an amount of 0.3%, cyanidin chloride ($C_{27}H_{31}O_6$), acetoin ($C_4H_8O_2$), β-ionone, and benzaldehyde. In animal tests, a decoction of *Rubus sachalinensis* Lev. was identified to alleviate fever as well as serve as a cordial and a diuretic. In Oriental medicine, the fruit is prescribed for patients suffering from fever, a cold, pneumonia, or cough.

As described above, the materials used in the present invention are obtained from herbs which grow naturally and are safe to the body, and young antler of deer. For use in the composition of health foods for the liver, the medicinal materials, fruits of *Lycium chinense* Miller, fruits of Macrocarpium officinale Sieb. et Zucc., young antlers of *Cornu cervi*, *Agastache rugosa* (Fischer et Meyer) O. Kuntze, young *Gastrodia elata blume*, *Amomum xanthioides* Wallich, fruits of *Cratagegus pinnatifida* Bge., Aquillaria Agallocha Roxburgh, *Inula Helenium* L., roots of *Pueraria lobat* Ohwi, seeds of *Cassia obtusifolia* L., and fruits of *Rubus sachalinensis* Lev. are dried and powdered. The powder mixture may be formulated in forms of tablets, granules or capsules, or used as materials of draughts or broths. Attentively, the medicinal material mixture may be extracted with hot water or organic solvents.

A better understanding of the present invention may be obtained in light of the following examples which are set forth to illustrate, but are not to be construed to limit the present invention.

EXAMPLE 1

Composition of Health Food for Promoting Blood Circulation

A composition of a health food for promoting blood circulation was prepared from the following components:

| | |
|---|---|
| Fruits of *Lycium chinense* Miller, | 9 wt % |
| young antlers of *Cornu cervi* | 9 wt % |
| *Agastache rugosa* (Fischer et Meyer) O. Kuntze, | 9 wt % |
| Roots of *Pueraria lobat* Ohwi | 9 wt % |
| Fruits of *Macrocarpium officinale* Sieb. et Zucc. | 8 wt % |
| *Gastrodia elata* blume | 8 wt % |
| *Amomum xanthioides* Wallich | 8 wt % |
| Fruits of *Cratagegus pinnatifida* Bge. | 8 wt % |
| Aquillaria Agallocha Roxburgh | 8 wt % |
| Inula Helenium L. | 8 wt % |
| Seeds of *Cassia obtusifolia* L.. | 8 wt % |
| Fruits of *Rubus sachalinensis* Lev. | 8 wt % |

In the following animal and human tests, the composition was assayed for the promotion of blood circulation.

Experimental Example 1

Effect of the Composition of Health Food on Blood Circulation (Animal Test)

To test the composition of the present invention for vasodilation effect, rats were subjected to vasoconstriction by injection of KCl to arteries of the hind limbs, followed by measuring the medicinal effect by use of physiography.

Before testing, Sprague-Dawley rats weighing about 20–25 g were adapted for one week or longer to an animal testing room which was maintained at a constant temperature and humidity. Rats that were observed to be healthy were selected for use in testing. 20 rats selected were divided to two groups of 10. To a test group, the composition was injected abdominally at doses of 0.14 mg per 250 g of body weight a day after being suspended in 9% saline. In the evening of the final day of the injection, a mixture of carbon tetrachloride (CC14) and corn oil in the proportions of 1:4 (v/v) was administered orally at a dose of 0.2 mL per kg of body weight to the test groups. To the other group, a gingko extract was injected for comparison. The results are given in Table 1, below. As apparent from the data of Table 1, the composition of health foods of the present invention is superior to the gingko extract in vasodilation effect against the vasoconstriction caused by the injection of 72.7 mM of KCl.

TABLE 1

Vasodilation Effect of the Composition and Ginko Extract against KCl-Caused Vasoconstriction

| Test Material | Contraction No. upon Injection of 72.7 mM KCl (%) | | | | Mean ± SD |
|---|---|---|---|---|---|
| | 1 | 2 | 3 | 4 | |
| Composition | 93.7 | 75.1 | 86.4 | 81.8 | 84.25 ± 6.78 |
| Gingko Extract | 47.3 | 60.2 | 52.8 | 66.1 | 56.60 ± 7.14 |

Experimental Example 2

Inhibitory Activity against Arteriosclerosis

The same male rats as selected in Experimental Example 1 were divided into three groups of 10. Only olive oil was fed to one group, serving as a positive control while cholesterol was orally administered at a dose of 40 mg/kg, along with cholecalcipherol at a dose of 1 U/kg, to the other groups once a day for 28 days, to induce arteriosclerosis. During each of 7 days after the administration, the composition of the present invention was orally administered at a dose of 0.250 g/kg to one of the two arteriosclerosis-induced groups, once a day. The same amount of physiologically active saline was administered in the same manner to the olive-fed group and the other arteriosclerosis-induced group serving as a negative control, separately.

At the final day of the experiment, the rats were fasted for 12 hours and anesthetized with urethane, followed by sampling blood from the abdominal aorta. Sera were obtained from the blood samples by centrifugation for 15 min at 3,000 rpm. Measurements were made of total cholesterol level and HDL-cholesterol content. Tryglyceride and calcium levels in the sera were evaluated with the aid of respective kits. The results are given in Table 2, below.

TABLE 2

Inhibitory Activity Against Arteriosclerosis (mg/100 mL)

| Group | Total Cholesterol | HDL-Cholesterol/ Total Cholesterol | Triglyceride | Ca |
|---|---|---|---|---|
| Positive Control | 72.1 ± 5.4 | 0.63 | 46.8 ± 8.01 | 15.9 ± 0.5 |
| Negative Control | 73.8 ± 4.2 | 0.45 | 53.9 ± 4.2 | 20.7 ± 0.8 |
| Composition-administered | 73.1 ± 9.1 | 0.69 | 45.1 ± 3.5 | 18.6 ± 1.4 |

Experimental Example 3

Analgesic Activity

One of the most widely used methods for screening analgesics is the acetic acid induced writhing test (Niemegeers, et al., Drug-Res. 1505 (1975)), in which drugs are subcutaneously injected to animals, 30 min after which a 1.0% acetic acid solution is abdominally injected at a dose of 0.1 mL/ 10 g per kg of body weight to induce a writhing state in which hind limbs are stretched, while from 10 min after the drug administration, writhing numbers are counted every 10 min.

In this experiment, the same rats as selected in Experimental Example 1 were divided into two groups of 10. Saline was administered to one control group. On the other hand, the composition of the present invention was suspended in 0.9% saline and administered at a dose of 20 mg/kg/day for two weeks to the other group. A writhing test as described above was performed at the same time once every seven days for two weeks. The results are given in Table 3, below. As apparent from the data of Table 3, the composition of health foods for promoting the circulation of blood have analgesic activity against the headache attributed to the disturbance of blood circulation.

TABLE 3

Writhing Test Results

| Group | Writhing No. | | Inhibitory Efficiency (%) | |
|---|---|---|---|---|
| | Fed for 1 week | Fed for 2 weeks | Fed for 1 week | Fed for 2 weeks |
| Control | 15.53 ± 8.71 | 18.24 ± 7.56 | — | — |
| Composition-administered | 11.25 ± 7.12 | 6.41 ± 4.76 | 36.2 | 67.5 |

As described hereinbefore, a composition of health food is provided for promoting the circulation of blood in accordance with the present invention. Made of natural medicinal herbs and young antler, the composition is safe to the body and exhibits excellent pharmaceutical effects of treating arteriosclerosis and alleviating the headache attributed to the disturbance of blood circulation.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A composition of health foods for promoting the circulation of blood, comprising:

9 wt % of *Lycium chinense* Miller, 9 wt % of young antlers of *Cornu cervi*, 9 wt % of *Agastache rugosa* (Fischer et Meyer) O. Kuntze, 9 wt % of *Pueraria lobat* Ohwi, 8 wt % of Macrocarpium officinale Sieb. et Zucc., 8 wt % of *Gastrodia elata blume,*

8 wt % of *Amomum xanthioides* Wallich, 8 wt % of *Cratagegus pinnatifida Bge.,*

8 wt % of Aquillaria Agallocha Roxburgh, 8 wt % of *Inula Helenium* L., 8 wt % of *Cassia obtusifolia* L., and 8 wt % of *Rubus sachalinensis* Lev.

* * * * *